May 2, 1972 J. H. ENNS Plant Pat. 3,145
NECTARINE TREE
Filed Sept. 10, 1970
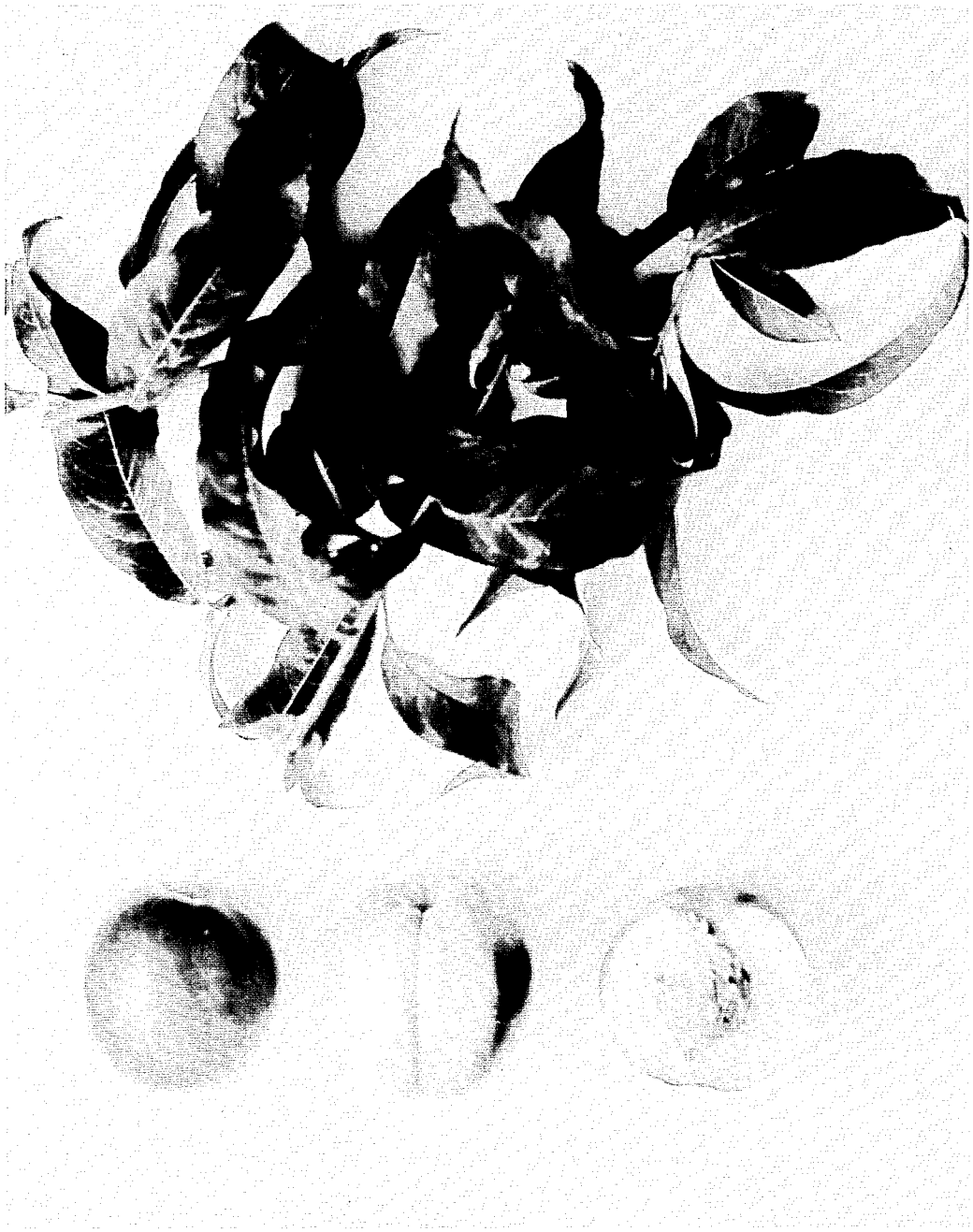
INVENTOR
John H. Enns
BY
Webster & Webster
ATTORNEYS

United States Patent Office

Plant Pat. 3,145
Patented May 2, 1972

3,145

NECTARINE TREE

John H. Enns, 39572 Road 64, Dinuba, Calif. 93618

Filed Sept. 10, 1970, Ser. No. 71,282
Int. Cl. A01h *5/03*
U.S. Cl. Plt.—41 1 Claim

ABSTRACT OF THE DISCLOSURE

A large, vigorous, spreading, vase-formed, open nectarine tree which is hardy and a regular and productive bearer of large, uniform, early ripening fruit having yellow skin substantially overspread with red, and yellow flesh with red near the stone; the latter being semifree.

ORIGIN OF THE VARIETY

The present variety of nectarine tree was discovered by me growing as a mutation or sport limb on a tree of the Star Grand II (United States Plant Patent No. 1,646) on my ranch located near Dinuba, County of Tulare, Calif.; the discovery having been made by reason of the fact that such sport limb was observed by me as having ripe fruit thereon before the remainder of the tree.

ASEXUAL REPRODUCTION OF THE VARIETY

Subsequent to discovery by me of the present variety of nectarine tree, I asexually reproduced it at my ranch, located as aforesaid, both by grafting and budding, and in maturity such reproductions ran true to the sport limb parent in all respects.

SUMMARY OF THE VARIETY

The present variety of nectarine tree is large, vigorous, spreading, vase-formed, open, hardy, and a regular and productive bearer of large, uniform fruit—of good to best eating quality—having yellow skin substantially overspread with red, and yellow flesh with red near the stone; the latter being semifree; the variety having general similarity in tree and fruit to the Star Grand II, but in particular being distinctively characterized, in comparison, by a ripening period approximately two weeks earlier, and which is about two to three days prior to the Early Sun Grand (United States Plant Patent No. 1,420).

BRIEF DESCRIPTION OF THE DRAWING

The drawing is a photographic reproduction in color of twigs with leaves, and individual fruit one of which is cut to expose the flesh and the stone.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Spreading.
- *Density.*—Open.
- *Form.*—Vase-formed.
- *Hardiness.*—Hardy.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.

- *Color.*—Brown.
- *Lenticels.*—Number—medium. Size—medium.

Leaves:
- *Size.*—Large to medium; average length (mature leaves)—6⅜"; average width (mature leaves)—1½".
- *Form.*—Lanceolate; acutely pointed.
- *Margin.*—Crenate.
- *Petiole.*—Medium length; medium thickness.
- *Glands.*—Average number—4; globose; usually positioned 2 on petiole, and 1 or 2 on blade.
- *Color.*—Top side—medium green (22–L–8). Underside—lighter green (21–I–7).

Flower buds:
- *Size.*—Medium.
- *Length.*—Medium.

Flowers:
- *Blooming period.*—Early to medium, as compared with other varieties. About with Sun Grand (United States Plant Patent No. 974).
- *Size.*—Large.
- *Color.*—Pink.

Fruit:
- *Maturity when described.*—Hard.
- *Date of first picking.*—June 18, 1970.
- *Date of last picking.*—June 28, 1970.
- *Size.*—Large; uniform; average diameter axially—2⅝"; average transversely in suture plane—2½".
- *Form.*—Uniform; symmetrical; globose to oblong.
- *Suture.*—Shallow.
- *Ventral surface.*—Rounded strongly.
- *Lips.*—Equal.
- *Cavity.*—Rounded; average depth—½"; average breadth—⅝"; markings—red.
- *Base.*—Rounded.
- *Apex.*—Short; rounded.

Skin:
- *Thickness.*—Thick to medium.
- *Texture.*—Medium.
- *Tendency to crack.*—None.
- *Down.*—Wanting.
- *Color.*—Yellow (9–L–5) substantially overspread with bright red (2–L–11 to 6–L–6 to 55–L–12); the lightest of which red shades from orange (9–L–8 to 9–L–11).

Flesh:
- *Juice.*—Moderate; rich.
- *Texture.*—Firm; meaty.
- *Fibers.*—Few.
- *Ripens.*—Evenly.
- *Flavor.*—Subacid.
- *Aroma.*—Distinct.
- *Eating quality.*—Good to best.
- *Color.*—Yellow (9–K–4, shading to 9–L–6), with red (2–K–7) near stone.

Stone:
- *Type.*—Semifree.
- *Size.*—Medium; average length—1¾"; average breadth—1$\frac{3}{16}$"; average thickness—⅞".
- *Form.*—Ovoid.
- *Hilum.*—Oblong.
- *Apex.*—Rounded.
- *Sides.*—Equal.
- *Surface.*—Regularly pitted from base to above center.
- *Ridges.*—Rounded.
- *Pitts.*—Elongated.
- *Ventral edge.*—Thick.
- *Dorsal edge.*—Full, with shallow groove.
- *Tendency to split.*—Slight.
- *Color.*—Tan (12–J–7).

Use: Market—local; long distance shipping.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, spreading, vase-formed, open, hardy, and a regular and productive bearer of large, uniform fruit—of good to best eating quality—having yellow skin substantially overspread with red, and yellow flesh with red near the stone; the latter being semifree; the variety having general similarity in tree and fruit to the Star Grand II, but in particular being distinctively characterized, in comparison, by a ripening period approximately two weeks earlier, and which is about two to three days prior to the Early Sun Grand.

No references cited.

ROBERT E. BAGWILL, Primary Examiner